United States Patent [19]

Fish et al.

[11] Patent Number: 4,634,462

[45] Date of Patent: Jan. 6, 1987

[54] METHODS OF AND APPARATUS FOR MONITORING PRECIPITATES IN METALLIC MATERIALS

[75] Inventors: Gordon E. Fish, Verona; Ryusuke Hasegawa, Morristown; Ernest D. Buff, Far Hills, all of N.J.

[73] Assignee: Allied Corporation, Morristown, N.J.

[21] Appl. No.: 690,061

[22] Filed: Jan. 9, 1985

[51] Int. Cl.⁴ .............................................. C03B 32/00
[52] U.S. Cl. .......................................... 65/29; 65/33; 65/158; 422/245
[58] Field of Search ................. 65/29, 158, 33; 422/245

[56] References Cited

U.S. PATENT DOCUMENTS

| | | | |
|---|---|---|---|
| 3,856,513 | 12/1974 | Chen et al. | 75/122 |
| 4,083,727 | 4/1978 | Andrus et al. | 65/33 X |
| 4,395,271 | 7/1983 | Beall et al. | 65/33 X |
| 4,396,721 | 8/1983 | Lawless | 65/33 X |
| 4,413,061 | 11/1983 | Kumar et al. | 65/33 X |

OTHER PUBLICATIONS

V. Ramanan and G. Fish, J. Appl. Phys. 53, 2273–2275 (1982).
Asahi et al. (Japan. J. Appl. Phys. 21, L116–118 (1982)).
Hasegawa and Ray (J. Appl. Phys. 49, 4174 (1978)).

Primary Examiner—Arthur Kellogg
Attorney, Agent, or Firm—Ernest D. Buff; Gerhard H. Fuchs

[57] ABSTRACT

A method and apparatus are provided for monitoring in situ the transformation of some fraction of a starting material to another material during the course of a thermal treatment. The starting material is heated to a preselected temperature and its permeability is measured. A signal is transmitted to an actuator, which indicates cooling of the material when a preselected or change therein is detected.

18 Claims, 3 Drawing Figures

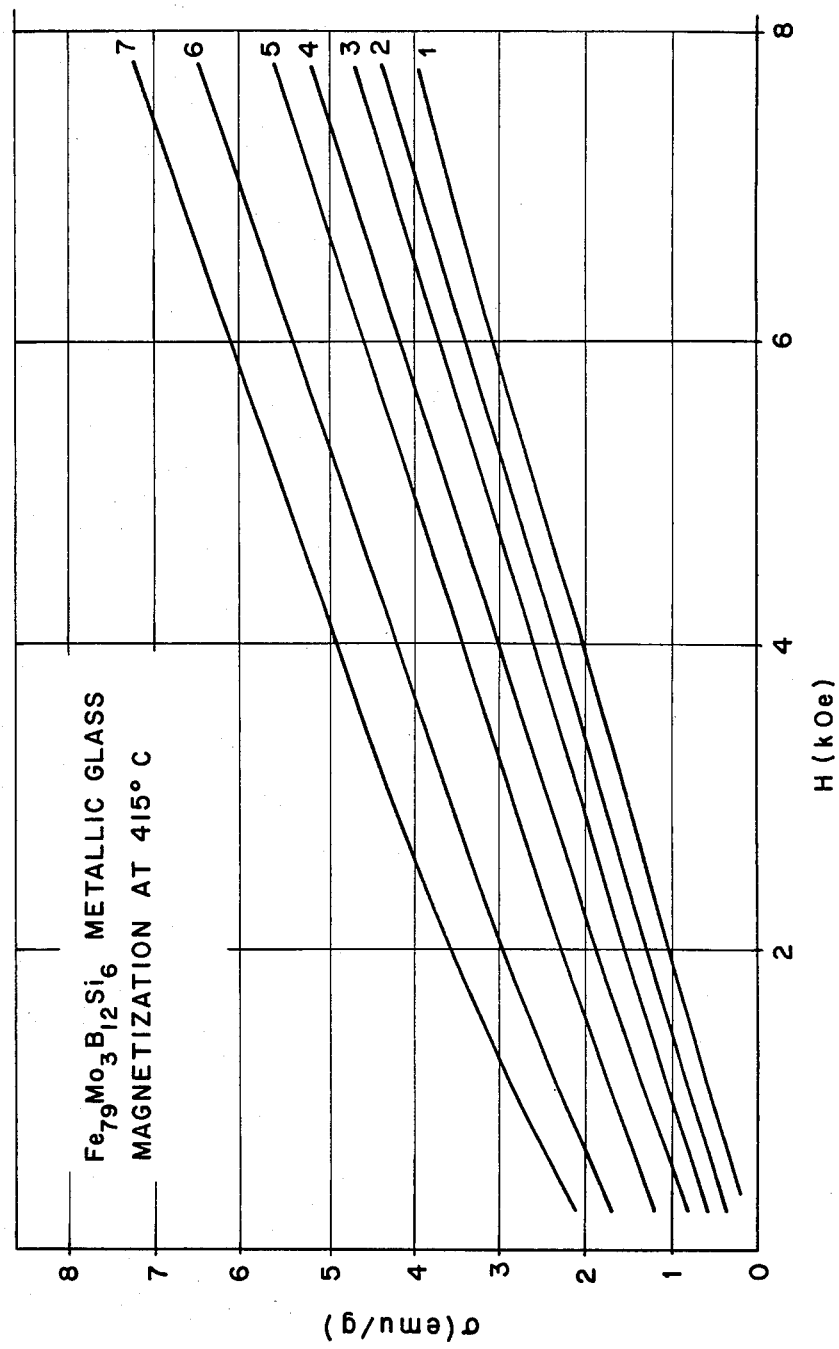

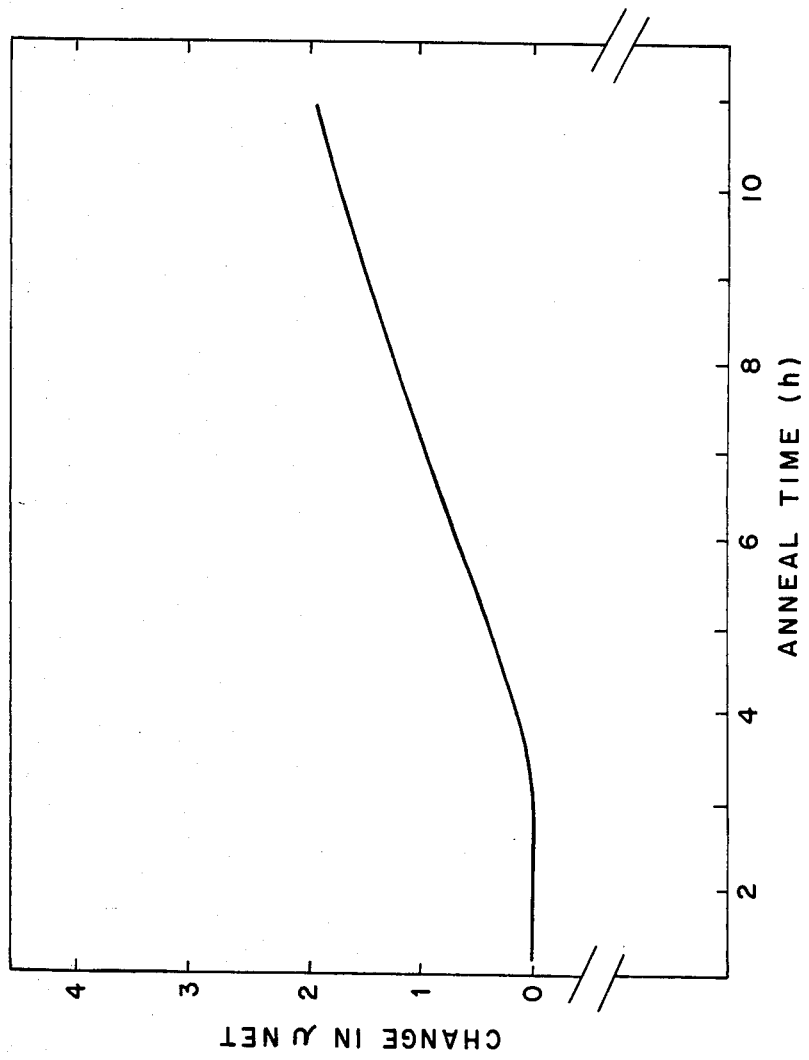

METHODS OF AND APPARATUS FOR MONITORING PRECIPITATES IN METALLIC MATERIALS

FIELD OF THE INVENTION

The invention relates to methods for in situ monitoring of the transformation of a portion of some matrix material into another material and, more particularly, to the monitoring of the controlled devitrification of ferromagnetic metallic glasses.

DESCRIPTION OF THE PRIOR ART

It is a frequent objective in materials processing to use heat treatment to induce the transformation of some fraction of the starting material into another material. The use of precipitation hardening in copper-beryllium alloys is a typical example.

Another example is provided by metallic glasses which are frequently heat treated to achieve optimized properties. Many metallic glasses are used in magnetic devices such as transformers, inductors, recording heads, and the like. For these applications, technical magnetic properties such as coercivity, remanence, a-c core loss, exciting power, and permeability can be enhanced markedly by such heat treatment, which is frequently carried out in the presence of an applied magnetic field.

An example wherein carefully controlled heat treatment is needed to achieve desired final properties is provided by iron-based ferromagnetic metallic glasses intended for high frequency applications. In these materials, it has been shown (see, e.g., R. Hasegawa, G. E. Fish, and V. R. V. Ramanan, Proc. 4th Intl. Conf. on Rapidly Quenched Metals (Sendai, 1981), Vol. II, p. 929) that heat-treatment which gives a controlled precipitation of about 1 vol. % of $\alpha$-Fe in a metallic glass such as $Fe_{75}Ni_4Mo_3B_{16}Si_2$ results in a substantial decrease in ac core loss. A transformer or inductor having a core with reduced ac core loss beneficially operates at higher efficiency with less heat produced.

As is known, metallic glasses (amorphous metal alloys) are metastable materials whose atoms lack any long-range order. X-ray diffraction scans of metallic glasses show only diffuse halos similar to those observed for inorganic oxide glasses. Metallic glasses are conventionally produced by techniques that allow a melt of the constituent chemical elements to be quenched at rates of $10^{5\circ}$ C./sec or higher. Typical metallic glasses and methods for production thereof are taught in U.S. Pat. No. 3,856,513 issued Dec. 24, 1974 to Chen, et al.

At elevated temperatures, metallic glasses are well-known to devitrify. That is, the starting material, which is homogeneous and has no periodic crystalline arrangement of its atoms, is transformed into an ensemble of crystalline particles having one or more chemical compositions. At an intermediate stage in the devitrification process, the material consists of an amorphous matrix containing a number of the aforesaid crystalline particles.

The thermal stability of metallic glasses is frequently characterized by techniques such as differential scanning calorimetry and differential thermal analysis. In these techniques, a sample is heated at a fixed rate of change of temperature with time, typically 10°–40° C./min, and the rate of transformation of the amorphous material into one or more crystalline materials is recorded. That temperature at which the transformation begins is defined as the crystallization temperature.

However, if a sample of metallic glass is held at a temperature below the crystallization temperature, thus determined, a devitrification process will begin after some length of time. This time becomes shorter as the temperature selected approaches the crystallization temperature.

Thus, for applications of metallic glasses, in which it is desired to produce a small amount of crystallinity in the glassy matrix, one can choose a temperature at which a heat treatment of reasonable and convenient duration produces the desired amount of precipitation. However, because of the inevitable variation of alloy chemistry and crystallization kinetics, samples from different batches of starting material will show variation in the degree of transformation for a given fixed temperature and duration of this heat-treatment.

A number of techniques are widely applied to the analysis of transformation reactions, including transmission electron microscopy (TEM), optical microscopy (OM), X-ray diffraction (XRD), and thermal techniques such as differential scanning calorimetry (DSC) and differential thermal analysis (DTA). Each of these techniques has certain disadvantages which preclude its use for in situ testing of finished articles. TEM requires that a sample be prepared with a thickness less than about 200 nm. OM requires that samples be prepared using conventional metallographic polishing and etching to reveal the character of the bulk of a sample. OM has the further limitation of only sensing transformed regions that are at least about 1 $\mu$m in size. XRD places stringent requirements on sample geometry, especially for examination of samples at elevated temperatures.

Thermal techniques have been used to sense the changes in specific heat that characterize transformation reactions. However, these changes are so small that measurements must be carried out under very carefully controlled conditions. For example, commercially available DSC instruments have been used for laboratory studies of crystallization of metallic glasses. (see, e.g., V. R. V. Ramanan and G.E. Fish, J. Appl. Phys. 53, 2273 (1982)). However, such studies are not adapted to the study of the initiation of transformation reactions, wherein the extent of transformation is small, owing to problems of the stability of the baseline in the instrumentation.

Furthermore, none of the above-mentioned techniques is adapted to the in situ monitoring of the extent of transformation during the course of heat treatment of an article which has been formed into a desired final size and with arbitrary shape.

Electrical and magnetic testing methods are widely practiced in the field of non-destructive evaluation. Magnetic particle techniques, such as the Magnaflux process, are primarily useful for detecting defects such as large cracks in ferromagnetic bodies and for detecting ferromagnetic inclusions in non-magnetic objects. The information thus provided identifies and localizes individual macroscopic defects but does not characterize an object in microscopic detail or in an averaged sense. That is, the Magnaflux process is not sensitive to small defects (size less than 1 $\mu$m) and does not provide an average determination of defect density.

Eddy current testing senses both electrical resistivity and magnetic permeability. Like magnetic particle methods, it is widely used for detecting gross defects.

Eddy current and four-probe resistivity methods have also been applied to systems in which electrical resistivity is known to be a reliable indication of another desired property. Examples of this include age-hardening of AlCuMg, AlMgSi and AlMgZu alloys, the austenite-martensite transformation in low carbon steels, and order-disorder transformations in Cu$_3$Au.

Magnetization and resistivity methods have been used previously to characterize metallic glasses which are substantially devitrified, that is to say, more than 10% transformed. Asahi et al. (Japan. J. Appl. Phys. 21, L116-118 (1982)) have studied the electrical resistivity of amorphous Fe$_{78}$Mo$_2$B$_{20}$, after the aloy is substantially devitrified. Hasegawa and Ray (J Appl. Phys. 49, 4174 (1978)) have used the rapid increase in magnetization at a given temperature in a non-isothermal experiment to identify the crystallization temperatures, as discussed above in the context of DSC, for Fe$_{100-x}$B$_x$ alloys. They identified, for example, crystallization temperatures of 565°, 655° and 680° K for x=12, 16 and 22 Neither of these techniques has been applied to determine transformations of a small fraction (less than about 10%) of a metallic glass into its devitrification products. Furthermore, these references teach the use of measurement of resistivity and magnetization during heating at a constant rate of increase of temperature (constant heating rate).

One of the most troublesome problems encountered in heat treatment of magnetic, alloys is the difficulty of preventing variations in magnetic properties among batches of material subjected to heat treatment. The varying response of different batches of material to a given heat treatment reduces the yield and increases the cost of the material. There remains a need in the art for a technique adapted to the in situ monitoring of articles in their characteristic form and shape during heat treatment that gives reliable indicatior of final properties.

SUMMARY OF THE INVENTION

The present invention provides a method and apparatus for monitoring in situ the transformation of some fraction of a starting metallic material into another material during the course of a thermal treatment. Generally stated, the thermal treatment is used to anneal a starting material and the method comprises the steps of heating the starting material to a preselected temperature; measuring the permeability of the material, and cooling the material. The annealing time is controlled in situ as a function of the permeability of the material, the latter being heated to a preselected temperature and maintained thereat until either a preselected permeability or change therein is detected.

Further, the invention provides apparatus for monitoring in situ the transformation of some fraction of a starting material into another material undergoing an anneal. The apparatus comprises heating means for heating the starting material to a preselected temperature; measuring means for measuring the permeability of the material; and cooling means for cooling the material. A signal means associated with the measuring means transmits an electrical signal to actuate the cooling means in response to a preselected change in the permeability of the material.

BRIEF DESCRIPTION OF THE DRAWINGS

The invention will be more fully understood and further advantages will become apparent when reference is made to the following detailed description of the preferred embodiments of the invention and the accompanying drawings, in which:

FIG. 2 is a graph containing a set of traces of the magnetization $\sigma$(emu/g) of the metallic glass Fe$_{79}$Mo$_3$B$_{12}$Si$_6$ measured as a function of applied field H(Oe) and at a temperature of 415° C. Trace 1 was taken immediately after the sample was heated from room temperature to a temperature of 415° C. The sample was held at 415° C. and traces were taken at times of 0.25, 0.5, 1, 2, 4 and 6 hours after trace 1; and FIG. 3 is a graph containing a trace of the change in net permeability of metallic glass Fe$_{79}$Mo$_3$B$_{12}$Si$_6$ measured at 430° C. as a function of anneal time. Permeability was determined for a toroidal sample of 13.5 cm mean path length containing about 8.5 g of metallic glass from the mutual induction of two sets of electrical windings on the toroidal sample.

DETAILED DESCRIPTION OF THE INVENTION

Figure 1:
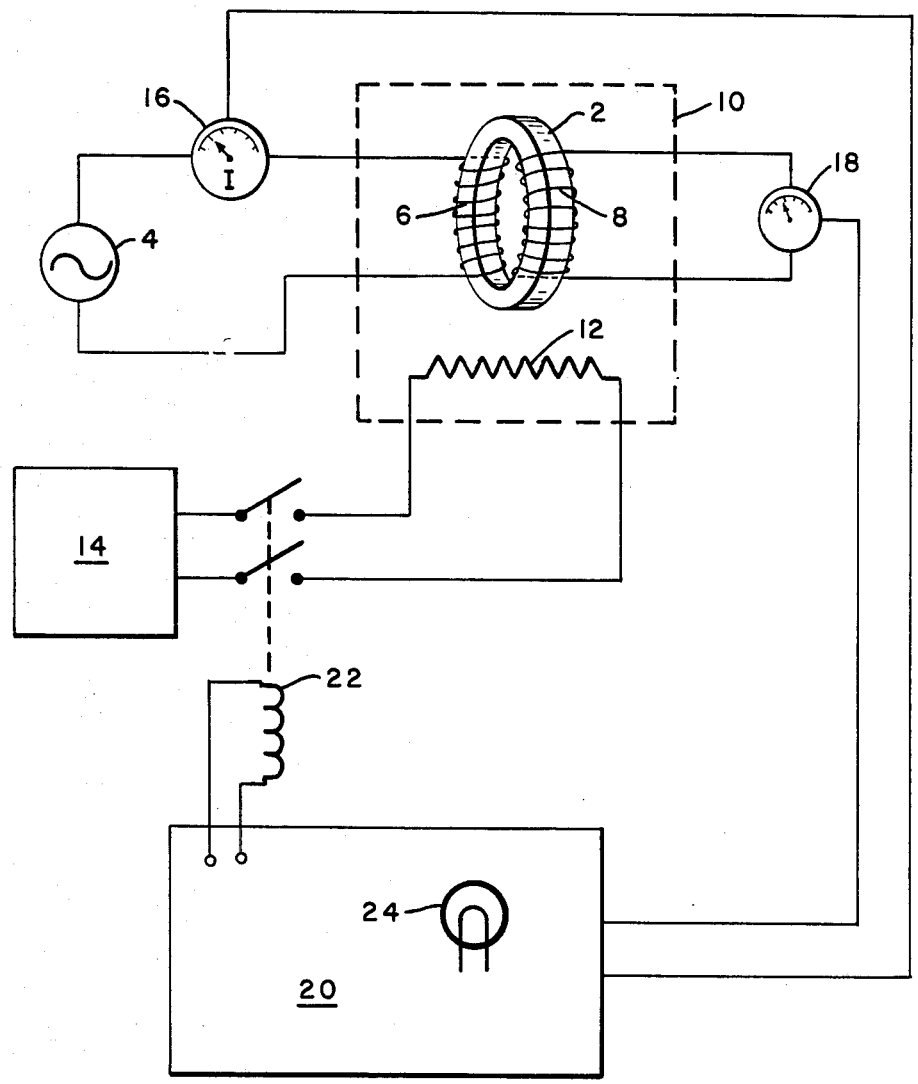
FIG. 1 is a schematic electrical diagram illustrating an apparatus for controlling the annealing of a core of magnetic material, the control being a function of the permeability thereof.

It is a principal objective of this invention to provide methods for the in situ monitoring of the extent of a transformation reaction induced by heat treatment of an article.

It is an advantage of the present invention that it can be practiced in the course of routine prqduction of commercial articles in their characteristic form, that it allows use of standard electrical testing equipment, and that it provides, during the course of a heat treatment, a semi-continuous characterization of the properties to be expected of the article in its finished form.

It is a further and more particular objective of this invention to provide methods for monitoring the controlled devitrification of ferromagnetic metallic glasses.

It is well-known in the art that materials may be classified generally as ferromagnetic, paramagnetic, or diamagnetic, on the basis of their response to an applied magnetic field H. For paramagnetic or diamagnetic materials, the magnetic induction in the material, B, is proportional to the applied magnetic field, H; that is, B=$\mu$H, where $\mu$ is the magnetic permeability relative to that of free space, in which $\mu$=1, B is in units of gauss and H is in units of oersteds. For paramagnets, ($\mu-1$) is typically of the order $10^{-3}$; for diamagnets, ($\mu-1$) is of the order $-10^{-6}$. Because of their low values of $\mu$, paramagnetic or diamagnetic materials are frequently considered to be non-magnetic. For ferromagnetic materials, the phenomenon of hysteresis implies that B is not strictly proportional to H. Thus, $\mu$ in the formula B=$\mu$H is a function which depends on H and the magnetic history of the sample. However, $\mu$ is much larger in ferromagnets than in paramagnets or diamagnets. In general, $\mu$ in ferromagnets is at least about 5 and can reach values as large as $10^5$–$10^6$ in some cases. Magnetic testing methods that sense $\mu$ are thus much more sensitive to the presence of a given quantity of ferromagnetic material than a like quantity of diamagnetic or paramagnetic material.

Furthermore, it is well-known that the spontaneous magnetization that gives rise to the large values of $\mu$ in ferromagnets decreases with increasing temperature reaching zero at the ferromagnetic Curie temperature $\theta_f$. Above this temperature, the permeability follows closely the Curie-Weiss law, $$\mu(T) = \frac{N\mu_{eff}^2}{3k_B(T-\theta_p)} + 1$$

where N is the number of effective magnetic species of effective magnetic moment $\mu_{eff}$, $k_B$ is the Boltzmann constant, T is the absolute temperature, and $\theta_p$ is the paramagnetic Curie temperature which is close to $\theta_f$.

In the special case in which a ferromagnetic material is very finely divided, with particle size less than about 10 nm, the material is said to be superparamagnetic and is characterized by a constant linear permeability $\mu \sim 10-50$ and by the absence of hysteresis. Such materials are distinguished from ordinary paramagnets by these large values of $\mu$ which disappear above the usual ferromagnetic Curie temperature.

The volume magnetic susceptibility $\chi$ of a material is defined by the relationship $\mu(H)=dB/dH=1+4\pi\chi$. For paramagnetic and diamagnetic materials, $\chi$, like $\mu$, is a constant. The magnetization $\sigma$(emu/g) is defined by the relationship $B=H+4\pi m\sigma$, where m is the mass density of the material in g/cm$^3$, B is in gauss, and H. is in oersteds.

Magnetic permeability or susceptibility can be conveniently measured using a number of techniques well known in the art. Among these are vibrating sample magnetometry and measurement of mutual induction of two electrical coils wound around a common core of magnetic material. For paramagnetic and diamagnetic materials, there results a linear relationship between applied field and resultant magnetization. For ferromagnets, there is an initial rapid increase in magnetization, but for higher applied field, the magnetization approaches a constant indicating saturation.

Most ferromagnetic metallic glasses are designed to have their Curie temperatures $\theta_f$ less than their crystallization temperatures $T_x$. This allows selection of an anneal temperature $T_a$ such that $\theta_f < T_a < T_x$. Thus, at $T_a$, the metallic glass is paramagnetic, and it has been found that the paramagnetic permeability $\mu_p$ changes only slightly during the course of an anneal. It has been assumed heretofore that magnetic monitoring of annealing does not have acceptable sensitivity. However, in many such metallic glasses, the crystalline products of devitrification have a Curie temperature higher than $T_a$ making them ferromagnetic at the temperature $T_a$.

Accordingly, the most preferred embodiment of this invention is the use of high temperature magnetic permeability measurement on a sample in which the starting material is non-magnetic but the transformed fraction is ferromagnetic. This provides the largest and most clear-cut change in signal.

Iron-based boron and silicon containing metallic glasses designed for high frequency ($f \geq 10$ KHz) applications in transformers, inductors, and the like, such as $Fe_{79}B_{16}Si_5$, $Fe_{75}Ni_4Mo_3B_{16}Si_2$, and $Fe_{79}Mo_3B_{12}Si_6$ fall into this category. Laboratory studies show that these materials may be optimally heat-treated at temperatures $T_a$ in the range 430°–460° C. for times $t_a$ of 1–4 hours. Such an anneal transforms about 1 vol. % of these glasses into crystallites having the body-centered cubic structure which contain predominantly iron. Such crystallites may either be distributed uniformly throughout the metallic glass or may be concentrated predominantly near or at either or both of the surfaces of the metallic glass. $T_a$ is greater than the ferromagnetic Curie temperature $\theta_f$ of these three metallic glasses (420°, 305° and 250° C. respectively), so that under the annealing condition, the glassy matrix is paramagnetic, with a Curie-Weiss like magnetic permeability $$\mu(T) = 1 + \frac{N\mu_{eff}^2}{3k_B(T-\theta_p)}$$

where $\theta_p$ is the paramagnetic Curie temperature which is close to $\theta_f$. However, body-centered cubic iron ($\alpha$-Fe) has $\theta_f=1043°$ K.=770° C. Thus, at Ta, the contribution of precipitates of $\alpha$-Fe will make the material superparamagnetic or weakly ferromagnetic, depending on the size of the crystallites. The net permeability $\mu_{net}$ measured is given by the expression $$\mu_{net}=(1-q)\mu_{matrix}+Q\mu_{precip}$$

where q is the volume fraction of precipitates and $\mu_{matrix}$ and $\mu_{precip}$ are the permeabilities of the matrix and precipitates, respectively. Assuming that $\mu_{precip}$ is of the order of 20–100, the values appropriate to an $\alpha$-Fe powder, transformation of 1 vol. % (q=0.01) of the glass ($\mu \approx 1$ at the annealing temperature) into $\alpha$-Fe will give a value of $\mu_{net}$ of 1.2–2 measured at the annealing temperature. This prediction was verified as described in detail below in Examples 1–2. For a completely glassy sample (q=0), $\mu_{net}=\mu_{matrix}=1$ at the annealing temperature. Hence, when annealing iron-based boron and silicon metallic glasses for high frequency applications, it is preferred that the change in permeability (e.g. the change in $\mu_{net}$), measured at the annealing temperature, has a magnitude ranging from about 0.1 to 4, and more preferably from about 0.2 to 1. Such a change in permeability is conveniently detected by measuring $\mu_{net}$ at the annealing temperature. Typically, for iron based boron and silicon containing metallic glasses, the preferred change in $\mu$net will be found to have occurred when $\mu_{net}$, measured at the annealing temperature, ranges from about 1.1 to 5, and more preferrably from about 1.2 to 2.

High frequency magnetic properties of Fe-based metallic glasses are generally improved by the presence of a volume fraction of 0.005 to 0.10 of discrete crystalline particles of the constituents of the metallic glass. Optimal magnetic properties are obtained with a volume fraction of about 0.01. The crystallites have sizes ranging from about 0.05 to 10 $\mu$m. The particles can have either a crystalline $Fe_3B$ structure or, more preferably, a body centered cubic structure. The particles can also comprise a mixture of particles wherein a first portion thereof has a body centered cubic structure, a second portion has a crystalline $Fe_3B$ structure, and a third portion, if present, has a mixed structure (eutectic structure) having regions with body centered cubic structure and with crystalling $F_3B$ structure.

The prior art method for control of heat-treatment of such metallic glasses is to heat-treat a number of samples of the metallic glass and measure magnetic properties such as permeability, core loss, remanence and coercivity which must fall into a certain range and then to select a suitable temperature and duration of anneal. However, the optimal temperature and duration of anneal will vary from one batch of starting material to the next. Accordingly, a series of measurements must be made to optimize the heat-treatment for each batch of material, or the overall yield of heat-treated samples having acceptable magnetic properties will be low.

In general, the optimal heat-treating temperature for a metallic glass is greater than its Curie temperature. Hence, at the annealing temperature, it is impossible to measure the magnetic properties which depend inherently on the material being in its ferromagnetic state, i.e., below its Curie temperature. It is the attainment of acceptable values for magnetic properties such as core loss, permeability, remanence, and coercivity, measured at the desired operating temperatures, that distinguishes acceptable material from unacceptable material.

In order to use the techniques described herein to monitor the extent of transformation of material being annealed, one would carry out preliminary experiments to determine what change in permeability measured at the annealing temperature occurred in material optimally heat-treated as evidenced by conventional testing of finished articles after the heat-treatment. Further articles would then be heat-treated until the predetermined change in permeability was seen to occur, then the heat-treatment would be terminated to produce finished articles having the desired end-use properties.

The techniques herein can also be used to monitor annealing of metallic glasses in which it is desired to preserve the glassy structure. Such an anneal is frequently used to enhance the magnetic properties of Fe- and Co-based alloys, particularly those containing at least one member selected from the group consisting of boron, silicon, carbon and phosphorus, when the same are intended for line frequency (50–400 Hz) applications. In this case, the permeability of the metallic glass would be monitored and if a change characteristic of the initial stage of devitrification were seen, positive indication could be given to an operator or the anneal could be terminated automatically and the metallic glass cooled to prevent further devitrification.

Two techniques were used to monitor magnetic permeability during annealing. In the first, the magnetization of a sample of the desired metallic glass was measured in a commercial vibrating sample magnetometer. The sample was heated and held at an annealing temperature $T_a$ and the high temperature permeability measured continuously during the anneal. The monotonic increase of permeability signaled the devitrification reaction as confirmed by X-ray diffraction and TEM which showed the presence of crystalline precipitates.

The second, and most preferred, measurement technique was to form a toroidal magnetic core by winding a sample of the metallic glass onto a toroidal ceramic form, to apply two sets of windings of copper wire with high temperature insulation to the core and then to measure the secondary voltage induced by a primary current as a function of time at temperature during the course of an anneal. Before any precipitation occurs, the paramagnetic permeability of the core caused only a slight increase in secondary voltage above what would be expected for an air-core transformer of the same toroidal geometry. As the anneal proceeded, precipitation occurred and $\mu_{net}$ increased, so that secondary voltage increased.

Referring to FIG. 1 there is shown a schematic electrical diagram illustrating an apparatus for controlling the annealing of a starting magnetic material having the form of a toroidal core 2. An ac current is supplied by a signal generator 4 to primary windings 6 wound about the core 2. An ac voltage is thereby induced in secondary windings 8. The core 2 with windings 6 and 8 is enclosed in a heating means comprising a furnace 10 with an electrical heating coil 12 powered by a power supply 14. A measuring means for measuring the permeability of core 2 comprises an ammeter 16 and a voltmeter 18, with which are determined, respectively, the primary current and secondary voltage. Signal means 20 determines the change in permeability of the core 2 from the ratio of secondary voltage from voltmeter 18 to primary current from ammeter 16. When a preselected permeability or change therein, as the case may be, is determined a signal is transmitted from signal means 20 to an actuating means operates upon receipt of said signal to initiate cooling of the core 2. In the embodiment shown, cooling is initiated when relay 22 opens and thereby interrupts the flow of electrical current from power supply 14 to heating coil 12. Signal means 20 further activates indicator means 24 when a preselected value of permeability is attained.

The net permeability $\mu_{net}$ of the sample was determined from measurement using the formula $$\mu_{net} = \frac{(1.267 \times 10^7) l_m V_2}{f I_1 N_1 N_2 A_m} - \frac{A_c}{A_m} + 1$$

where $l_m$ is the mean circumference of the toroid in cm, $V_2$ is the induced secondary voltage in V, f is the excitation frequency in Hz, $I_1$ is the primary exciting current in A, $N_1$ and $N_2$ are the number of primary and secondary turns, respectively, $A_c$ is the cross-sectional area in cm$^2$ enclosed by the windings, and $A_m$ is the cross-sectional area in cm$^2$ of the sample (metallic glass). The sensitivity of the measurement is increased by making the ratio $A_m/A_c$ as close to 1 as practical, i.e., filling the windings completely with the metallic glass. The amplitude of secondary voltage $V_2$ is enhanced by proper choice of f, I, $N_1$ and $N_2$. In the case of randomly oriented ferromagnetic precioitates in a paramagnetic matrix, the value of $\mu_{precip}$ is approximately constant for applied fields up to at least about 8kA/m. Hence values of $N_1$ and $I_1$ can be chos n to increase $V_2$ by giving a peak magnetic field $H_{peak} = 8$ kA/m using the formula $H_{peak} = \sqrt{2} N_1 I_1 / l_m$, where $I_1$ is the rms primary current in A and $l_m$ is the mean magnetic path length in m. However, for cores with practical dimensions (e.g. less than 20 centimeters OD) the value of $H_{peak}$ is generally limited by the maximum number of turns $N_1$ that can be accommodated on the core and by the need to limit $I_1$ to prevent excessive ohmic heating in the primary windings.

$V_2$ is further increased by using as many secondary turns $N_2$ as practical for a given size of core and by increasing f. It is generally found that f of the order of 1 kHz is preferred. A higher frequency decreases $\mu_{net}$ and, hence, $V_2$.

This method has the clear advantage in that it can be practiced on magnetic cores of any size fabricated into final form. Even though one is ultimately interested in magnetic properties at operating temperatures of, say, 100° C. or below, the control of annealing can be done at high temperature because of the correlation between presence of crystallites which changes the high temperature permeability and good properties at the operating temperatures of interest. Inevitable minor variations in processing parameters or alloy composition changes the nominal anneal necessary for good properties. This method allows in situ compensation for these deviations. The measurements are simple enough to be done with standard laboratory signal generator and volt meters.

It is known that annealing of ferromagnetic metallic glasses causes changes in their Curie temperatures. The initial change is irreversible and occurs upon stress relaxation afer a very brief interval at a temperature of about 300° C. Some additional change in Curie temperature, generally less than 5° C., can occur during further annealing. In addition, if partial devitrification occurs with crystalline products of composition different from that of the matrix, the Curie temperature of the matrix changes in accordance with the change in the matrix composition. These changes in Curie temperature thus change the contribution of the matrix to the observed permeability $\mu_{net}$ in accord with the Curie-Weiss law. For cases in which the annealing temperature $T_a$ is within about 30° C. of the Curie temperature $\theta_p$, a correction to the observed permeability must be made using measured values of $\theta_p$.

The following examples are presented to provide a more complete understanding of the invention. The specific techniques, conditions, materials and reported data set forth to illustrate the principles and practice of the invention are exemplary and should not be construed as limiting the scope of the invention.

EXAMPLE 1

The magnetization of a sample of metallic glass having the composition $Fe_{79}Mo_3B_{12}Si_6$ with Curie temperature $\theta_f$ of 250° C. and mass of about 60 mg was measured as a function of anneal time at 415° C. using a Princeton Applied Research Model 155 Vibrating Sample Magnetometer with high temperature oven accessory. Temperature was monitored with a Chromel-Alumel thermocouple in close proximity to the sample. The sample was heated to 415° C., then held at that temperature. The applied magnetic field was held at 8 kOe and the resultant magnetization recorded continuously, except for several brief intervals during which a complete trace of magnetization versus applied field was obtained for the alloy at various stages of the transformation. The magnetization versus applied field curve obtained immediately upon reaching 415° C. (Trace 1 of FIG. 2) was completely linear, as is characteristic of a paramagnetic material such as this metallic glass above its Curie temperature.

As the anneal proceeded, the magnetization at 8 kOe increased monotonically, and the magnetization versus applied field trace became non-linear, having a linear component of magnetization characteristic of the paramagnetic matrix and a non-linear component of magnetization characteristic of ferromagnetic material approaching saturation (Traces 2-7 of FIG. 2) The slope of the paramagnetic component changed only slightly, whereas the ferromagnetic component increased significantly due to the presence of precipitated α-Fe in the sample. Samples of the metallic glass annealed for various times at 415° C. were also examined using X-ray diffraction and TEM. These confirmed tne presence of precipitates of α-Fe in the amorphous matrix.

EXAMPLE 2

A sample of about 8.5 g of metallic glass ribbon having the composition $Fe_{79}Mo_3B_{12}Si_6$ was wound onto a torodial ceramic form. Two sets of electrical windings having about 220 turns each of high temperature polyimide insulated Cu wire were then applied. One set was used to apply an alternating magnetic field at about 0.95 kHz along the circumferential direction of the toroid. The resulting alternating change in magnetization of the metallic glass induced a voltage in the other set of windings. The sample was heated in a tube furnace to 425° C. An exciting voltage was applied to give a sinusoidal applied field of 1.5 Oe maximum amplitude; the resultant induced voltage was monitored as a function of time at temperature. The change in net permeability of the sample calculated from the induced voltage is shown as a function of time in FIG. 3. The increase in permeability shown was caused by precipitation of α-Fe in the sample, which was confirmed by X-ray diffraction.

Having thus described the invention in rather full detail, it will be understood that this detail need not be strictly adhered to but that further changes and modifications may suggest themselves to one skilled in the art, all falling within the scope of the invention as defined by the subjoined claims.

What is claimed is:

1. A method for annealing a starting material composed of a magnetic, metallic glass wherein a portion of said starting material is transformed into a transformed material having a magnetic permeability different from that of said starting material, comprising the steps of:
   a. heating said starting material to a preselected temperature;
   b. measuring the magnetic permeability of said material while at said temperature;
   c. maintaining said starting material at said preselected temperature until a preselected change in magnetic permeability thereof is detected; and
   d. cooling said material when said preselected change in magnetic permeability has been detected.

2. A method as recited in claim 1, wherein said starting material is a member selected from the group consisting of paramagnetic and diamagnetic material.

3. A method as recited in claim 1, wherein said starting material is a member selected from the group consisting of superparamagnetic or ferromagnetic material.

4. A method as recited in claim 1, wherein said transformed material consists essentially of discrete crystalline particles of the constituents of said amorphous metal alloy.

5. A method as recited in claim 4, wherein said amorphous metal alloy is iron or cobalt based and contains at least one member selected from the group consisting of boron, silicon, carbon and phosphorus.

6. A method as recited in claim 5, wherein said amorphous metal alloy is iron based and contains boron and silicon.

7. A method as recited in claim 4, wherein a substantial portion of said particles have a body-centered cubic crystal structure.

8. A method as recited in claim 4, wherein a portion of said discrete particles have a crystalline $Fe_3B$ structure.

9. A method as recited in claim 4, wherein said particles occupy a volume fraction of said starting material ranging from about 0.005 to 0.10.

10. A method as recited in claim 1, wherein said starting material is ferromagnetic at room temperature, said preselected temperature is greater than the Curie temperature of said starting material, and said transformed material is ferromagnetic with a Curie temperature is greater than said preselected temperature.

11. A method as recited in claim 10, wherein said starting material is maintained at said preselected temperature until a preselected change in said permeability is detected, said preselected change in permeability resulting in a permeability ranging from about 1.2 to 5.

12. A method as recited in claim 11 wherein said preselected change in permeability results in a permbability ranging from about 1.2 to 2.

13. A method as recited in claim 10, wherein said preselected change in permeability has a magnitude ranging from about 0.1 to 4.

14. A method as recited in claim 10, wherein said preselected change in permeability has a magnitude ranging from about 0.2 to 1.

15. Apparatus for annealing a starting material composed of a magnetic, metallic glass comprising:
   a. heating means for evenly heating said starting material to a preselected temperature;
   b. measuring means for continously or intermittently measuring the magnetic permeability of said material during said heating;
   c. cooling means for cooling said material;
   d. signal means associated with said measuring means for sensing said magnetic permability and for transmitting an electrical signal in response to a preselected change in said magnetic permeability; and
   e. actuating means operative upon receipt of said signal to actuate said cooling means.

16. Apparatus as recited in claim 15, further comprising indicator means operative upon receipt of said signal to indicate that a change in permeability has occurred.

17. A method for annealing a starting material composed of a magnetic, metallic glass, wherein a portion of said starting material is transformed into a transformed material having a magnetic permeability different from that of said starting material, comprising the step of:
   a. heating said starting material to a preselected temperature;
   b. continuously or intermittently measuring the magnetic permeability of said material while at said temperature;
   c. maintaining said starting material at said preselected temperature until a preselected magnetic permeability thereof is detected; and
   d. cooling said material when said preselected permeability is detected.

18. A method for annealing a starting material composed of a magnetic, metallic glass without effecting transformation of a portion of said starting material into a transformed material having a permeability different from that of said starting material,
   a. heating said starting material to a preselected temperature;
   b. continuously or intermittently measuring the magnetic permeability of said material while at said temperature;
   c. maintaining said starting material at said preselected temperature for a preselected period of time;
   d. remeasuring the magnetic permeability of said material at the conclusion of said preselected period of time; and
   e. cooling said material of which a preselected change in magnetic permeability has not been detected.

* * * * *